United States Patent [19]

Herman

[11] 4,424,055
[45] Jan. 3, 1984

[54] IRRIGATION AND ASPIRATION SYRINGE

[76] Inventor: Wesley K. Herman, 7311 Pleasant View Dr., Dallas, Tex. 75231

[21] Appl. No.: 332,332

[22] Filed: Dec. 18, 1981

[51] Int. Cl.³ ............................................. A61M 1/00
[52] U.S. Cl. .................................................. 604/36
[58] Field of Search ............... 128/276, 763, 764, 765, 128/766, 220, 221, 224, 234, 218 R, 218 D, 218 P, 218 PA, 218 S, 215, 216; 604/35, 36, 38, 27, 28, 181, 294

[56] References Cited

U.S. PATENT DOCUMENTS 2,860,635 11/1958 Wilburn ........................... 128/218 S
3,656,472 4/1972 Moura ................................ 128/763
4,263,911 4/1981 McCormack et al. ............. 128/276

FOREIGN PATENT DOCUMENTS 2125041 11/1972 Fed. Rep. of Germany ...... 128/220
595802 7/1925 France ............................... 128/220

Primary Examiner—John D. Yasko
Attorney, Agent, or Firm—Richards, Harris & Medlock

[57] ABSTRACT

An irrigation and aspiration syringe is provided for one-handed operation. A cylindrical syringe barrel has a first axial control grip projecting from the nozzle end of the syringe. An outer tubular member surrounds the syringe barrel and is connected to the rod of a plunger fitted within the syringe cartridge. A second axial control grip is affixed to the outer tubular member. Aspiration is effected by oppositely directed axial forces applied to the first and second control grips with the thumb and forefinger of one hand.

8 Claims, 5 Drawing Figures

IRRIGATION AND ASPIRATION SYRINGE

TECHNICAL FIELD

This invention relates to an irrigation and aspiration syringe, and more particularly to such a syringe having control grips on the syringe barrel and an outer sleeve for one-handed operation.

BACKGROUND ART

A cataract is a cloudiness or opacity which develops in the lens of the eye which is normally clear and transparent. A person with impaired vision due to a cataract may have his vision improved through a combination of cataract surgery and proper corrective lenses.

An ophthalmologic surgeon may elect one of several different surgical procedures for removing a lens that has a cataract. Intracapsular cataract extraction is a technique for the removal of the entire cataract, including its capsule, in one piece. Extracapsular cataract extraction and phacoemulsification and aspiration are two surgical techniques that involve the removal of the opacified portions of the lens, while the clear posterior capsule which was the original support for the lens is left in place. In the extracapsular technique, the clear capsule will provide support as well for the implanted plastic intraocular lens. In this fashion, the intraocular lens can be placed behind the iris rather than supported on it or in front of it. Current research suggests that this is a more favorable position for an implant, both for optical and for eye health reasons.

In the extracapsular cataract extraction technique, an incision is made in the eye large enough to deliver the nucleus of the lens separately. The incision is then closed and irrigation and aspiration are required to remove the softer cortex or peripheral cataract portions. The lens nucleus is frequently very hard and requires removal by this planned extracapsular technique. However, if the lens nucleus is soft enough, the center of the cataract called the nucleus can be emulsified with ultrasound. The hardness of a lens nucleus which clinically is usually related to the density or brunescence of the nucleus determines whether a cataract can be emulsified or whether it requires planned extraction. In the ultrasound technique, a small incision of approximately three millimeters is made in the front of the eye, and a very tiny needle connected to an ultrasonic generator is inserted into the eye. The ultrasonic generator vibrates the needle tip at up to 40,000 cycles per second. This ultrasonic action cuts away and emulsifies the cataract. The emulsified lens may then be withdrawn through a regulated suction through the end of a needle.

Regardless of which extracapsular surgical technique of nucleus removal is employed, irrigation and aspiration is required to remove the peripheral lens cataract (cortex). Current medical instumentation available for irrigation and aspiration is either a conventional syringe or a sophisticated mechanical irrigation and aspiration unit. The conventional syringe requires two hands to operate, but there is often a requirement in cataract surgery to have one hand free for other tasks. It is not considered safe, convenient or comfortable for a surgeon to use both hands for the operation of the conventional syringe. The operation of mechanical irrigation and aspiration units requires highly sophisticated personnel and additional equipment such as a system to provide a vacuum for the suction. The present state of the art phacoemulsification instruments are expensive and the cost to the patient for each use is significant, while the damage potential to the eye in an inexperienced hand is great.

A need has thus arisen for an irrigation and aspiration instrument which can be operated with a single hand in surgery. In addition, a need has arisen for an irrigation and aspiration surgical device which is simpler to operate, is useful in less technologically developed areas, and reduces the risk of damage to the eye.

DISCLOSURE OF THE INVENTION

In accordance with the present invention, a compact irrigation and aspiration instrument is provided for one-handed operation, particularly in extracapsular cataract surgery. The improved irrigation and aspiration instrument includes a syringe barrel having a first control grip extending upwardly from the barrel, and a second control grip affixed to an outer sleeve fitted over the barrel and attached to the plunger. A needle is attached to the syringe having an opening at the end of the needle for aspirating material through the needle into the barrel of the syringe. A vacuum may be produced by the aspiration and irrigation instrument by using the control grips with one hand to slide the outer sleeve axially away from the end of the barrel connected to the needle and thus retract the plunger. The contents of the syringe may be expelled upon removal of the instrument from the patient's eye with one-hand operation by using the control grips to slide the sleeve axially toward the end of the barrel connected to the needle. An irrigation solution is admitted through an inlet port of a cylindrical sleeve surrounding the needle, the sleeve extending to a discharge opening near the tip of the needle.

In another embodiment of the invention, a first control grip extends upwardly from the barrel of the syringe, and an outer sleeve surrounds the barrel and has a curved handle to fit the palm of the hand and a second control grip along the side of the sleeve opposite the first control grip on the barrel. The syringe is opened to aspirate fluid by using the first and second control grip with one hand to withdraw the plunger from the barrel.

BRIEF DESCRIPTION OF THE DRAWINGS

A more complete understanding of the present invention and its advantages will be apparent from the following Detailed Description, taken in conjunction with the accompanying drawings in which.

DETAILED DESCRIPTION

Figure 1:
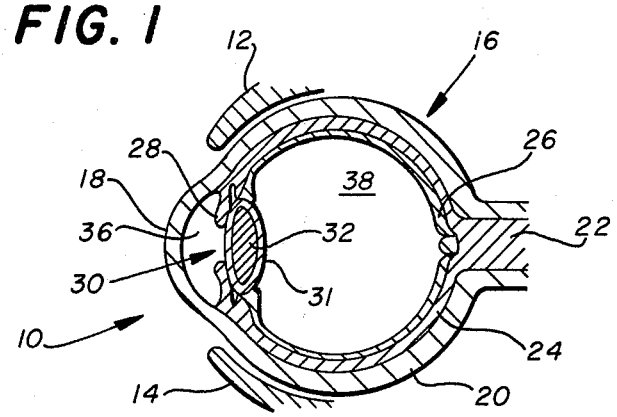
FIG. 1 is a cross-sectional schematic view of a human eye.

FIG. 1 illustrates a cross-sectional schematic view of the human eye, generally identified by the reference numeral 10. The eye 10 is shown surrounded in front by the upper lid 12 and lower lid 14. The eye 10 may be viewed as consisting of a large sphere 16 with the segment of a smaller sphere, the cornea 18, in front.

The eye 10 is composed of three layers. The first layer is the tough, white outer coat including the cornea 18 and the sclera 20, which covers approximately the posterior five-sixths of the surface and extends to the external sheath of the optic nerve 22. The middle layer is the choroid 24, the thin, pigmented vascular coat of the eye extending posteriorly to the optic nerve 22. The third layer is the retina 26.

The iris 28 is the circular pigmented membrane behind the cornea 18, and the iris 28 is perforated by the pupil 30. The lens 32 is a double-convexed normally transparent body held in place by an elastic lens capsule 31. The aqueous humor 36 fills the space between the cornea 18 in front and the lens 32 in the rear. The vitreous humor 38 is a clear, jelly-like substance filling the space behind the lens 32.

Figure 2:
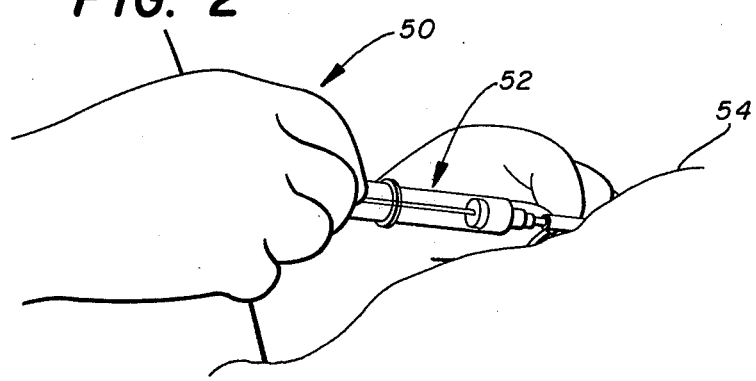
FIG. 2 illustrates a conventional irrigation and aspiration syringe in extracapsular cataract surgery.

FIG. 2 illustrates the position of the opthalmologic surgeon's hands 50 in relation to a conventional surgical aspiration syringe 52 and the surgically draped patient 54. High magnification in ophthalmologic microsurgery requires great stability and maximum proprioceptive control of the patient's eye and head position at all times during surgery. The mid-air hand position required for the aspiration technique with a conventional syringe 52 is a precarious portion of extracapsular surgery. Two hands are required to stabilize the aspiration syringe 52 within the patient's eye. The one hand proximate the needle of the syringe 52 is necessary for near control and patient proprioception, and the other hand is necessary for applying suction and occasionally reverse suction while irrigating and aspirating the cortical cataractous material.

Figure 3:
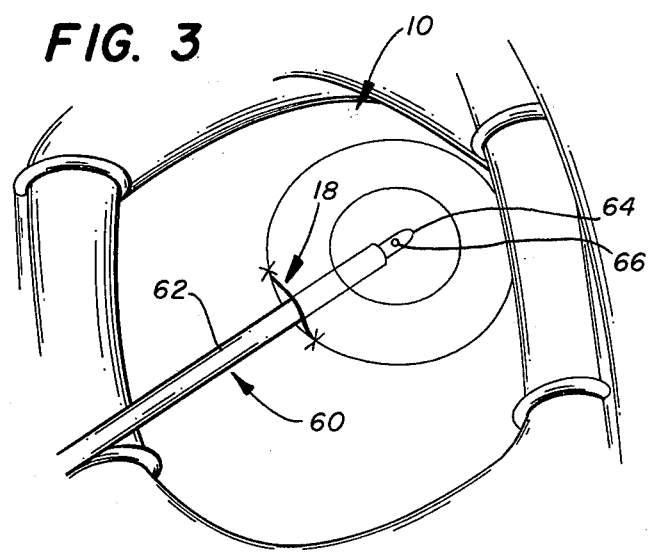
FIG. 3 is a magnified view of the needle of an irrigation and aspiration syringe in use in cataract surgery.

FIG. 3 is a low magnification photograph of the surgeon's view while performing the previously described irrigation and aspiration technique illustrated in FIG. 2. A needle 60 connected to the irrigation and aspiration syringe 52 is inserted in an incision made on the edge of the cornea 18. The tip of the needle 60 includes an outer sleeve portion 62 fitted about an inner cylindrical member 64 to allow the flow of a balanced intraocular irrigation solution to irrigate the eye 10. An opening 66 is formed in the inner member 64 for aspirating the cortical cataractous material from the eye 10.

Figure 4:
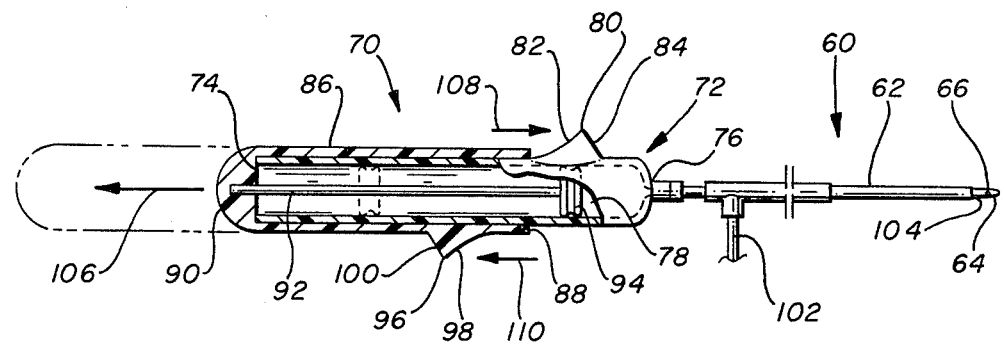
FIG. 4 is a partially cut away side elevation view of one embodiment of the present invention.

FIG. 4 illustrates an irrigation and aspiration syringe 70 of the present invention. A generally cylindrical syringe barrel 72 extends from an opening 74 located at the rear of the barrel 72 to a nozzle 76 located at the front of the syringe barrel 72. The cortical cataractous material aspirated from the eye is withdrawn into a chamber 78 of the syringe wheel 72 through the nozzle 76. A first control grip 80 is positioned on the syringe barrel 72 at a point proximate the nozzle opening 76. The control grip 80 includes a forward sloping surface 82 extending upwardly to join a rearward sloping surface 84.

An outer sleeve 86 is dimensioned to slide over the outer cylindrical surface of the syringe barrel 72. The sleeve 86 includes an open end 88 for receiving the syringe barrel 72 and extends to a closed end 90. A rod 92 is secured in the closed end 90 and extends to a plunger 94 dimensioned to closely fit inside the hollow chamber 78 of the syringe barrel 72. The outer sleeve member 86 has a second control grip 96 extending from its outer surface at a point proximate the open end 88. The control grip 96 includes a rearward sloping surface 98 extending from the surface of the sleeve 86 to intersect a forward sloping surface 100.

The nozzle 76 of the irrigation and aspiration syringe 70 is connected to the needle 60. A balanced intraocular irrigation solution is connected to the inlet port 102 of the needle 60. The irrigation solution flows through the needle 60 to a discharge opening 104 to irrigate the eye during surgery. The flow of the irrigation solution is regulated by gravity pressure by adjusting the height of the bottles containing the solution.

In operation, the needle 60 is inserted beneath the cornea 18 in the manner shown in FIG. 3. Irrigation solution flows continuously into the needle through the input port 102 through a discharge port 104. The cortical cataractous material is aspirated from beneath the cornea 18 by vacuuming the material into the chamber 78 of the syringe 70 through the opening 66 of the needle 60. The syringe 70 may be used to aspirate material from the eye by single handed operation, leaving the surgeon's other hand free to use a second instrument, if necessary. The syringe 70 may be grasped with the thumb resting on the forwardly inclined surface 82 of the first control grip 80. The index finger rests against the rearward sloping surface 98 of the second control grip 96. Suction is applied by moving the outer sleeve 86 in the direction indicated by the arrow 106, causing the plunger 94 to draw material up into the chamber 78. The thumb applies a directive force to the forward sloping surface 82 in the direction of the axis of the syringe barrel 72 indicated by 108. The index finger applies a force to the rearward sloping surface 98 in the opposite direction along the axis of the syringe barrel 72, as indicated by the arrow 110. The suction pressure may be stopped by reversing the movement of the outer sleeve 86, so that the outer sleeve 86 moves forward in the direction towards the nozzle 76 of the syringe. This feature enables the surgeon to have precise one-handed control to break the suction pressure if the instrument engages the iris 28 or the posterior lens capsule 31. The contents of the syringe 70 may be emptied by drawing the needle 60 from the eye and sliding the plunger 94 forward by moving the outer sleeve 86 in the direction towards the nozzle 76 of the syringe, opposite to that indicated by arrow 106. In discharging the contents from the syringe 70, the outer sleeve may be moved in the forward direction by reversing the position of the thumb and forefinger on the control grips 80 and 96, such that the thumb is placed on the rearward inclined surface 84 and the index finger rests on the forward inclined surface 100.

Figure 5:
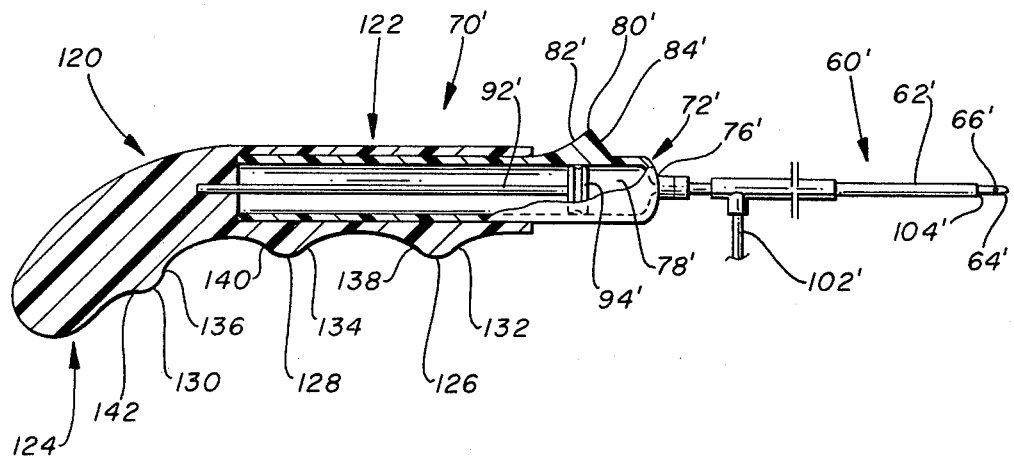
FIG. 5 is a partially cut away side elevation view of an alternate embodiment of the present invention.

FIG. 5 illustrates an alternate embodiment of the present invention, generally identified by the reference numeral 70'. Many of the component parts of the syringe 70' are substantially identical in construction and function to component parts of the syringe 70. Such identical component parts are designated in FIG. 5 with the same reference numerals utilized hereinbelow in the description of the syringe 70, but are differentiated therefrom by means of a prime (') designation. In this embodiment, the plunger 94' is connected through the rod 92' to an outer sleeve 120 having a first generally cylindrical section 122 dimensioned to fit about the cartridge 72' and a second curved handle section 124 to conform to the palm of the hand. The finger control grips 126, 128 and 130 are provided on the side of the outer sleeve 120 opposite that of the control grip 80' for the thumb. The control grips 126, 128 and 130 have generally rearward sloped first surfaces 132, 134 and 136, respectively, and forward sloped surfaces 138, 140 and 142, respectively. The irrigation and aspiration syringe 70' may be operated in a similar manner to that described above for the syringe 70. The outer sleeve 120 is retracted from the cartridge 72' to draw the plunger in 94' and provide suction to the opening 66'.

While the irrigation and aspiration syringe of the present invention has been described in detail herein, it will be evident that various and further modifications are possible without departing from the scope and spirit of the present invention.

I claim:

1. An irrigation and aspiration syringe comprising:
    a hollow cylindrical cartridge extending to a nozzle at one end and an enlarged opening at the opposite end;
    means for controlling the axial movement of said cartridge;
    a needle secured to the nozzle and having a first passage in fluid communication with the hollow chamber of the cylindrical cartridge and a second passage for connection to a source of irrigation fluid for irrigation;
    a plunger having a disk dimensioned to closely engage and slide within the hollow cylindrical cartridge, and a rod for controlling the movement of the disk within said cartridge;
    an outer sleeve dimensioned to receive said cartridge; said sleeve including an open end for receiving the open end of said cartridge and means for connecting said rod of said disk to the opposite end of said sleeve; and
    means for controlling the axial movement of said outer sleeve, whereby said means for controlling axial movement of said cartridge and said means for controlling the axial movement of said outer sleeve permit selective axial movement of said outer sleeve relative to said hollow cylindrical cartridge with one hand while maintaining the needle in the desired position for irrigation and aspiration, movement of said sleeve along said cartridge to withdraw said plunger from said cartridge creating a vacuum at said nozzle end for aspirating material into said hollow chamber of said cartridge, movement of said sleeve along said cartridge to move said plunger into said cartridge reducing the vacuum at the nozzle to control the rate of aspiration.

2. The irrigation and aspiration syringe of claim 1, wherein said means for controlling the axial movement of said cartridge is a first control grip extending from said cartridge proximate said nozzle opening, and said means for controlling the axial movement of said outer sleeve comprises a second control grip extending from said sleeve opposite said control grip of said cartridge.

3. The irrigation and aspiration syringe of claim 2, wherein a said first control grip includes a first control surface sloping towards said nozzle opening of said syringe cartridge, and said second control grip includes a first control surface sloping away from said nozzle end of said syringe cartridge, whereby oppositely directed axial forces may be applied to said control grips for separating said syringe cartridge and said outer control sleeve for aspirating material into said cartridge.

4. The irrigation and aspiration syringe of claim 1, wherein said outer sleeve extends to a closed end dimensioned to form a hand grip to conform to the palm of the hand.

5. The irrigation and aspiration syringe of claim 4, wherein said means for controlling axial movement of said cartridge is a first control grip extending from said cartridge proximate said nozzle, and said means for controlling the axial movement of said outer sleeve is a plurality of control grips extending from the side of said outer sleeve opposite said first control grip, whereby said plurality of control grips conform to the surgeon's hand.

6. An irrigation and aspiration syringe for use in irrigation and aspiration of an eye, comprising:
    a hollow cylindrical cartridge extending at one end to a nozzle and at the opposite end to an enlarged opening;
    a first control grip extending from said cartridge proximate said nozzle opening for controlling the axial movement of said cartridge;
    a needle secured in a fixed relationship to said cartridge defining a first passage therein in fluid communication with said nozzle opening and defining a second passage for connection to a source of irrigation fluid for irrigating the eye;
    a plunger having a disk shaped member dimensioned to closely engage and slide within said hollow cylindrical cartridge and a rod for controlling the movement of the disk in said cartridge;
    an outer tubular member dimensioned to receive said cartridge, said tubular member including an open end for receiving the open end of said cartridge and means for connecting said rod of said disk member to said tubular member; and
    a second control grip extending from said tubular member opposite said first control grip of said cartridge, whereby said first and second control grips may be operated with one hand to permit selective axial movement of said outer tubular member relative to said hollow cylindrical cartridge in both directions by the hand while maintaining the needle in the desired position in the eye for irrigation and aspiration, movement of said tubular member in the opposite direction from the nozzle end of said cartridge withdrawing said plunger from said cartridge to provide a vacuum at said nozzle end for aspirating material through the first passage into said cartridge, movement of said tubular member in the direction toward the nozzle end of said cartridge moving said plunger into said cartridge to reduce the vacuum at the nozzle end, selective movement of said tubular member relative to the cartridge permitting control of the aspiration rate with one hand.

7. The irrigation and aspiration syringe of claim 6, wherein said first control grip includes a first surface sloping in the direction of said nozzle opening of said syringe cartridge, and said second control grip includes a surface sloping in the direction away from said nozzle end of said syringe cartridge, whereby oppositely directed axial forces may be applied to said control grips for separating said syringe cartridge and said tubular member for aspirating material into said cartridge.

8. The irrigation and aspiration syringe of claim 6 and further comprising:
    said first control grip including a second control surface sloping in the direction away from said nozzle opening of said syringe cartridge; and
    said second control grip including a second control surface sloping towards said nozzle end of said syringe cartridge, whereby opposing axial forces may be applied to said control grips for stopping the vacuum present at the nozzle end of said cartridge and for expelling aspirated material from said cartridge.

* * * * *

UNITED STATES PATENT AND TRADEMARK OFFICE
CERTIFICATE OF CORRECTION

PATENT NO. : 4,424,055
DATED : January 3, 1984
INVENTOR(S) : Wesley K. Herman

It is certified that error appears in the above—identified patent and that said Letters Patent is hereby corrected as shown below:

Column 1, line 42, change "brunescence" to
 --brunesence--.

Column 3, line 48, change "wheel" to --barrel--.

Signed and Sealed this

Tenth Day of April 1984

[SEAL]

*Attest:*

*Attesting Officer*

GERALD J. MOSSINGHOFF

*Commissioner of Patents and Trademarks*